(12) United States Patent
Grawe et al.

(10) Patent No.: US 9,173,843 B2
(45) Date of Patent: Nov. 3, 2015

(54) CRYSTALLINE ACTIVE INGREDIENT MICROPARTICLES, METHOD FOR PRODUCING THE SAME AND USE THEREOF IN DRUGS

(75) Inventors: Detlef Grawe, Kleinromstedt (DE); Sabine Gliesing, Jena (DE); Robert Eilers, Jena (DE)

(73) Assignee: Jesalis Pharma GMBH, Jena (DE)

( * ) Notice: Subject to any disclaimer, the term of this patent is extended or adjusted under 35 U.S.C. 154(b) by 651 days.

(21) Appl. No.: 13/058,168

(22) PCT Filed: Jun. 30, 2009

(86) PCT No.: PCT/EP2009/004724
§ 371 (c)(1),
(2), (4) Date: Feb. 8, 2011

(87) PCT Pub. No.: WO2010/015298
PCT Pub. Date: Feb. 11, 2010

(65) Prior Publication Data
US 2011/0144071 A1 Jun. 16, 2011

(30) Foreign Application Priority Data
Aug. 8, 2008 (DE) .......................... 10 2008 037 025

(51) Int. Cl.
A61K 31/58 (2006.01)
A61K 31/56 (2006.01)
A61P 5/00 (2006.01)
C07J 53/00 (2006.01)
C07J 1/00 (2006.01)
C07J 7/00 (2006.01)
C07J 3/00 (2006.01)
A61K 9/16 (2006.01)
H04R 5/00 (2006.01)

(52) U.S. Cl.
CPC .............. *A61K 9/1694* (2013.01); *A61K 9/1652* (2013.01); *H04R 5/00* (2013.01)

(58) Field of Classification Search
None
See application file for complete search history.

(56) References Cited

U.S. PATENT DOCUMENTS

| 4,263,011 A | 4/1981 | Huguenard et al. |
| 4,961,890 A | 10/1990 | Boyer |
| 5,091,187 A | 2/1992 | Haynes |
| 5,145,684 A | 9/1992 | Liversidge et al. |
| 5,202,129 A | 4/1993 | Samejima et al. |
| 5,389,382 A | 2/1995 | List et al. |
| 5,622,938 A | 4/1997 | Wong |
| 5,811,609 A | 9/1998 | Vilstrug et al. |
| 5,858,410 A | 1/1999 | Muller et al. |
| 6,290,931 B1 | 9/2001 | Grawe et al. |
| 7,148,212 B2 | 12/2006 | Grawe et al. |
| 7,388,096 B2 | 6/2008 | Gleeson et al. |
| 2002/0127278 A1 | 9/2002 | Kipp et al. |
| 2003/0175187 A1 | 9/2003 | Schiewe et al. |
| 2003/0216360 A1 | 11/2003 | Grawe et al. |
| 2005/0139144 A1 | 6/2005 | Muller et al. |
| 2005/0214228 A1 | 9/2005 | Begon et al. |
| 2006/0115539 A1 | 6/2006 | Prasch |
| 2009/0087492 A1* | 4/2009 | Johnson et al. ............... 424/489 |
| 2009/0142407 A1 | 6/2009 | Lizio et al. |
| 2009/0227546 A1 | 9/2009 | Sandrone et al. |
| 2009/0297565 A1 | 12/2009 | Mueller et al. |

FOREIGN PATENT DOCUMENTS

| EP | 0 454 138 A2 | 10/1991 |
| EP | 1 214 076 B1 | 11/2003 |
| EP | 1 625 849 A1 | 2/2006 |
| EP | 1 497 308 B1 | 9/2006 |
| WO | WO 01/14036 A1 | 3/2001 |
| WO | WO 01/15701 A1 | 3/2001 |
| WO | WO 2005/009375 A2 | 2/2005 |
| WO | WO 2008/084312 A2 | 7/2008 |

OTHER PUBLICATIONS

Braga et al. "Crystal Polymorphism and Multiple Crystal Forms," Structu. Bond 2009, vol. 132, pp. 25-50.*
chemhelper.com "recrystallization" (http://chemhelper.com/recryst2.html, cached wayback machine Mar. 15, 2006) no pagination.*
Pharmaceutical International, "Controlling Crystallisation of Pharmaceutical Ingredients" http://www.pharmaceutical-int.com/article/pharmaceutical-crystallisation.html, date Dec. 6, 2006, no pagination.*
Teipel, Ulrich, et al., "Less deviation," *Mineral Processing*, vol. 52, pp. 45-53 (2011).
Thibert, Roch, et al., "Micronization of Pharmaceutical Solids," *MML Series*, vol. 1, pp. 327-347 (1999).

(Continued)

*Primary Examiner* — Mina Haghighatian
*Assistant Examiner* — Erin Hirt
(74) *Attorney, Agent, or Firm* — Patterson Thuente Pedersen, P.A.

(57) ABSTRACT

A method for producing highly crystalline and stable microparticles of an active substance with a very narrow size distribution. The microparticles being crystallized out of a suspension made of primary particles of the active substance, a solution of the active substance, a non-solvent for the active substance and inert formed pieces. The resulting microparticles hare are highly stable largely independent of the physiochemical properties of the active substance and can be especially suitable for fast release dosage forms of pharmaceuticals.

27 Claims, 6 Drawing Sheets

(56) References Cited

OTHER PUBLICATIONS

Nuernberg, E., "Darstellung und Eigenschaften pharmazeutisch relevanter Spruehtrocknungsprodukte, eine Uebersicht," *Acta Pharm. Tech.*, vol. 26, No. 1, pp. 40-67 (1980).

Kerč, J., et al., "Micronization of drugs using supercritical carbon dioxide," *International Journal of Pharmaceutics*, vol. 182, pp. 33-39 (1999).

Steckel, H., et al., "Micronizing of steroids for pulmonary delivery by supercritical carbon dioxide," *International Journal of Pharmaceutics*, vol. 152, pp. 99-110 (1997).

Beckmann, "Seeding the Desired Polymorph: Background, Possibilities, Limitations, and Case Studies", Organic Process Research & Development, 2000, vol. 4, pp. 372-383.

Bernstein, "Polymorphism in Molecular Crystals" textbook, Oxford, 2002, 4 pages.

\* cited by examiner

CRYSTALLINE ACTIVE INGREDIENT MICROPARTICLES, METHOD FOR PRODUCING THE SAME AND USE THEREOF IN DRUGS

PRIORITY CLAIM

The present application is a National Phase entry of PCT Application No. PCT/EP2009/004724, filed Jun. 30, 2009, which claims priority from German Application Number 102008037025.8, filed Aug. 8, 2008, the disclosures of which are hereby incorporated by reference herein in their entirety.

FIELD OF THE INVENTION

The present invention is generally directed to a method for producing crystalline microparticles of an active substance, in which the active substance is crystallized from a suspension of primary particles, solvent, non-solvent and inert formed pieces. Specifically, the present invention is directed to a method for producing a solid form of particles of active substance and the microparticles of active substance and solid forms of medicaments that contain the microparticles, obtainable by these methods.

BACKGROUND OF THE DISCLOSURE

For high efficacy and bioavailability of pharmaceuticals, it may be necessary to reach high serum levels of active substances in a very short time, which requires dosage forms that are released as quickly as possible. However, rapid release is often hampered by the poor water-solubility of active substances.

The kinetics of release and therefore the bioavailability of pharmaceuticals is, apart from the disintegration properties of the pharmaceutical form, dependent primarily on the particle size, the particle size distribution and the crystallinity of the active substance. To speed up the release of poor soluble active substances, they are usually micronized, i.e. the solid active substances are comminuted to particle sizes in the micrometer range. Jet mill procedures are usually used for this.

However, micronization, the micronizates produced thereby and use thereof in dosage forms have disadvantages with respect to undesirable amorphization and from the point of pharmaceutical processability. Thibert and Tawashi: "Micronization of pharmaceutical solids", MML-Series, 1999, Vol. 1, Chap. 1, p. 328-347. The amorphization is more pronounced, i.e. the crystallinity is lower, the finer the granulometry, and thus the higher the energy input required for milling. Therefore it is in fact very fine-grained micronizates, such as are required for rapid release and pulmonary applications, e.g. with an average grain size of 1-1.5 µm, that have a high amorphous fraction, which for certain active substances can be 5-20% or higher, i.e. the crystallinity is 80-95 wt. % or lower.

The partial amorphization in micronization is associated with chemical and physical destabilization of the active substance. Subsequent agglomerations and recrystallizations can further impair release from the pharmaceutical form. These disadvantages become even more apparent, the finer the granulometry, as is desired for rapid release. Therefore, stability problems can arise in the case of micronizates, both as active substance and in the pharmaceutical form in contact with the excipients. Furthermore, micronizates tend to become highly charged, to form dust and to have poor pourability and flowability, so that processing to the pharmaceutical form is only possible in special, expensive processes, e.g. fluidized-bed wet granulation.

For very rapid release, in the case of poorly soluble active substances, particle sizes are required that cannot be achieved by micronization processes, or can be achieved but only together with severe amorphization. Agglomeration and crust formation that already occur during the grinding operation can make grinding more difficult. Furthermore, micronizates have as a rule a relatively wide grain size distribution. For rapid release kinetics, however, a narrow grain size distribution is desirable, with both the proportions of nanoparticles and the proportions of larger particles being minimized.

Micronizates can be combined with excipients by means of preformulations so that some disadvantageous properties, such as poor processability, are improved. DE 103 25 989 A1 describes active substance—excipient micropellets, which are produced on the basis of micronizates by fluid-bed granulation. This technology is, however, linked inseparably with the aforementioned disadvantages, which arise from the destructive, high-energy grinding process and the attainable granulometry. Moreover, these coarse-grained granules are not suitable for low-dose and ultra-low-dose formulations owing to the required uniformity of content of the active substance.

Very fine crystalline particles can be produced by wet-grinding methods with and without additives, for example surfactants, hydrocolloids or sugar, in ball mills or high-pressure homogenizers, as described for example in U.S. Pat. No. 5,145,684, U.S. Pat. No. 5,091,187, and U.S. Pat. No. 5,858,410. In this case, with an extremely high specific energy input, coarse particles are ground to nano size. However, this process takes a long time, and often requires multiple passes of the suspension through the milling chamber. In addition to the high costs of the apparatuses and possible amorphization, contamination through abrasion and wear of the milling equipment is a further disadvantage.

To avoid these disadvantages, to achieve rapid release, active substances can be spray-dried completely amorphously or can be embedded as a molecular dispersion in hydrophilic, polymeric excipients. E. Nürnberg in "Darstellung and Eigenschaften pharmazeutisch relevanter Sprühtrocknungsprodukte", Acta Pharm. Techn., 26(1), p. 40-67, 1980. This is described in European Patent Application 04103837 A1 with concrete active substances and with reference to specific pharmaceutical applications. These forms have the disadvantage, however, that the good solubility properties are obtained at the expense of considerable risks in chemical stability and with correspondingly high loading also in physical stability.

A special case of molecular embedding for speeding up release is the formation of inclusion complexes with cyclodextrins. However, this method is associated with molecular geometry suitable for complexing and therefore is not of universal application.

Other technology comprises spraying an organic solution of active substance on a carrier, as described for example in DE 19652196 A1. This can take place during fluid-bed granulation for the production of tablet granules or alternatively by spray-drying as a heavily loaded preformulation. The disadvantages of this technology comprise the frequent complete or partial amorphization in the spray-drying of solutions of active substances or else in the production of an unstable crystalline modification. Even with the heavily loaded preformulations described, rapid release is not automatically achieved, as the layers of active substance on the micronized carrier do not dissolve more quickly than comparable active substance micronizates. This technology has its strengths rather in the achievement of good uniformity of content for low-dose or ultra-low-dose formulations and better processing of poorly micronizable active substances. Moreover, the use of flammable solvents increases the technological costs in the production process.

An alternative to micronization and to the use of amorphous or crystalline spray-formulated combinations of active substances and excipients is the production of crystals with a grain size distribution that is adapted to the required release behaviour, by crystallization in a device for wet grinding followed by temperature oscillation, as described in EP 1497308 B1. The particles obtainable by this method are indeed crystalline, but as a rule do not reach the particle size that is necessary for very rapid release. Thus, as a rule not even the average grain size of micronizates is achieved. Furthermore, in fact during crystallization of extremely fine particles from highly supersaturated solutions, the fine primary particle granulometry is lost again through concomitant agglomeration. For forms with very rapid release, this technology has therefore reached its limits.

DE 10214031 A1 describes a precipitation method for the production of micro- and nanoparticles for fast dissolving as well as pulmonary dosage forms. The active substance is dissolved in a solvent and then precipitated with a non-solvent in the presence of a crystal growth inhibitor. The disadvantage of this method is that once again, because of the rapid phase transfer, analogous to spray-drying, amorphous or metastable phases are usually produced. This applies mainly to poorly crystallizable active substances with high configurative entropy, where the stable crystal form is kinetically disadvantaged. The presence of the crystal growth inhibitor means that a phase transfer to the stable modification during the production process is more difficult or is even prevented. This is associated with imponderable stability problems in the pharmaceutical form. Another disadvantage is that despite inhibition of growth, the precipitable grain size is strongly dependent on the physicochemical properties of the active substance and is not always sufficiently fine for very rapid release.

Other methods of production of suspensions of fine-grained particles of active substance by precipitation are described in U.S. Pat. No. 5,389,382, US Patent Application 2005/0139144 and US Patent Application 2002/0127278. Here, however, crystal growth is limited by the precipitation conditions (e.g. mixture ratio), the presence of stabilizers, or by corresponding energetic post-treatment in a high-pressure homogenizer.

Another precipitation method for the production of nanoparticles of active substances is described in DE 10 2005 053 862 A1. Here, just before or in a high-energy zone of small volume (ultrasound cell, shearing clearance of a high-pressure homogenizer, rotor-stator clearance in a colloid mill), the dissolved active substance is mixed with a non-solvent and is precipitated. These high-energy wet-grinding devices modified as precipitation reactors operate continuously by the through-flow principle. In contrast to the pure grinding process, this combination can produce particle sizes well into the nano range. However, this method also has the disadvantage that the equipment is very expensive, and contamination problems (e.g. with sonotrode material) often arise. These arrangements are not suitable for active substances that crystallize slowly or with difficulty, or for those that pass through unstable, e.g. amorphous intermediate phases. Therefore this method is only suitable for organic compounds that crystallize sufficiently rapid.

Another method for producing micro- and nanoparticles is the precipitation using supercritical carbon dioxide. Kerc, et al.: "Micronization of drugs using supercritical carbon dioxide", Int. J. Pharm. 182, 1999, 33-39; Steckel, et al.: "Micronizing of steroids for pulmonary delivery by supercritical carbon dioxide", Int. J. Pharm. 152, 1997, 99-110. However, these methods are very expensive in terms of apparatus and technology, because they involve working with supercritical gases.

A fundamental disadvantage of the aforementioned spray-drying and precipitation methods is due to their nature. The majority of active substances are of a polymorphic character, i.e. they are able to crystallize in more than one crystal modification. For pharmaceutical uses, however, with few exceptions, the thermodynamically most stable crystal modification is preferred. According to Ostwald's Rule of Stages, the higher-energy, and thus less stable modifications, amorphous-crystalline mixed forms or even the purely amorphous form, e.g. regularly in the case of spray-drying of solutions, form preferentially from solutions, especially in the case of rapid process kinetics. Phase transformations to the stable modification are difficult to control, even if they occur at all within a reasonable period of time. Because of the high levels of supersaturation, precipitation methods are naturally extremely rapid phase transition processes, and this can lead to problems in the reproducible production of a thermodynamically stable crystal form, especially as this transformation, which can overlap with the precipitation process or may also take place later, can have a considerable adverse effect on the grain size achieved.

SUMMARY OF THE DISCLOSURE

The present invention is directed to overcoming the disadvantages of the prior art and to provide a method that supplies, with inexpensive equipment, particles of active substance in the micrometer range, which are highly crystalline, are in the most stable crystal modification and have a very narrow particle size distribution, so that they are suitable for very rapid and complete release of medicaments. The present invention is also directed to a method for the production of a fast release solid form of particles of active substance. The present invention is also directed to providing the crystalline microparticles of active substance obtainable by these methods, and an associated solid form.

A method for producing crystalline microparticles of active substance according to an embodiment of the present invention comprises preparing a suspension from primary particles of the active substance, a solution of the active substance, non-solvent for the active substance and inert formed pieces. The suspension is mixed to cause the active substance to crystallize out of the suspension. The active substance is separated in the form of product particles and subsequently dried. The resulting primary particles and the product particles are crystalline, are in the most stable crystal modification of the active substance, have a crystal surface area of 3-10 $m^2/g$ and the size distribution of the primary and product particles is in each case $d_{50}$=1-2 μm, $d_{99}$<6 μm and $d_{100}$<12 μm.

The method, according to an embodiment of the present invention, surprisingly supplies, crystalline microparticles that have a very narrow particle size distribution, a high crystal surface area, and that are in the most stable crystal modification largely independent of the physicochemical properties of the active substance. According to an embodiment of the present invention, the resulting microparticles of active substance are especially suitable for fast release dosage forms of pharmaceuticals.

According to an embodiment of the present invention, the method for the production of a solid form of particles of active substance adding a hydrophilic, pharmaceutically acceptable excipient is added to the separated product particles before drying. In this configuration, the obtained solid form of particles of active substance comprises a hydrophilic excipient and the crystalline microparticles of the substance.

The method can also be used to produce microparticles of active substance and solid forms of particles of active. The solid form of particles of active substance of rapid release of the active substance without aggregation as individual particles on contact with water, largely independent of the grain size of the solid form. Furthermore, the solid form according to an embodiment of the present invention has superior pharmaceutical processing properties, as it is coarser than the usual micronizates, has better flowability and does not become charged electrostatically. As a result, the solid form can be further processed to dosage forms very economically, e.g. by dry-mixing processes in tablet production. In particular, the solid form of particles of active substance according to an embodiment of a present invention is especially suitable for low-dose and ultra-low-dose applications.

The above summary of the various representative embodiments of the invention is not intended to describe each illustrated embodiment or every implementation of the invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE FIGURES

The invention can be completely understood in consideration of the following detailed description of various embodiments of the invention in connection with the accompanying drawings, in which.

While the invention is amendable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE FIGURES

The term "active substance", within the meaning of the invention, is a pharmaceutical active substance, i.e. a substance that shows a physiological effect when it is absorbed in sufficient amount by the body of an organism.

In the method according to an embodiment of the present invention, the active substance to be crystallized is dissolved in a suitable solvent or a mixture of solvents. The active substance is then mixed with a non-solvent for the active substance and with primary particles of the active substance and inert formed pieces. The resulting supersaturation of the active substance causes crystallization of active substance in the form of product particles and creating a crystallization suspension. The obtained product particles of active substances are crystalline, have a very narrow particle size distribution and are in the same size range as the added primary product as result the available crystal surface area of the primary particles and the additional surface area of the formed pieces that are present and partial break-up of the particles of active substance (primary and product particles) when they collide with the inert formed pieces as a result of mixing. Moreover, the product particles obtained by a method according to an embodiment of the present invention are in the most thermodynamically stable crystal modification of the active substance.

The particle size distribution (grain size distribution) is measured by means of a laser diffraction, which provides a distribution curve of the particle sizes (System Sympatec Helos, RODOS dry disperser). $d_x$ means that x volume percent (vol. %) of the particles have a diameter that is smaller than the stated value. Thus, at a $d_{50}$ value of 1 μm, 50 vol. % of the particles have a diameter smaller than 1 μm (micrometer). When the $d_{10}$, $d_{99}$ or $d_{100}$ is 2 μm, 10, 99 or 100 vol. % of the particles have a diameter smaller than 2 μm.

The primary particles are used in an embodiment of the method and product particles obtained from the method can comprise a size distribution of $d_{50}$=1-2 μm, $d_{99}$<6 μm and $d_{100}$<12 μm. This means that 50 vol. % of the particles used and of the particles obtainable by the method have a diameter less than 1 to 2 μm, 99 vol. % of the particles have a diameter less than 6 μm and 100 vol. % of the particles have a diameter smaller than 12 μm. The $d_{99}$ value of less than 6 μm and the $d_{100}$ value of less than 12 μm show that, relative to the $d_{50}$ value, there is only a very small proportion of coarse particles. According to an embodiment of the present invention, the size distribution is $d_{50}$=1.2-1.8 μm, $d_{99}$<6 μm and $d_{100}$<12 μm. According to another embodiment of the present invention, the size distribution is $d_{100}$<8 μm. The nanofractions of the crystalline microparticles obtainable can also be minimized. Therefore size distribution can comprise $d_{20}$<0.8 μm and can comprise 0.6-0.75 μm according to an embodiment of the present invention. Also, a size distribution can comprise $d_{10}$<0.7 μm can alternatively comprise 0.35-0.65 μm according to another embodiment of the present invention. The size distribution can comprise $d_5$<0.4 μm and comprise 0.25-0.35 μm according to another embodiment of the present invention. The above size distributions relate, in each case independently of one another, to the primary particles and the product particles. The values for $d_{20}$, $d_{10}$ and $d_5$ can occur individually or in combination with the values given above for $d_{50}$, $d_{99}$ and $d_{100}$. For example, it is preferable for the size distribution to be $d_{10}$=0.35-0.65 μm, $d_{50}$=1-2 μm and $d_{100}$<8 μm.

Another advantage of the method according to the invention is the high crystallinity of the product particles obtainable. Highly crystalline or crystalline particles, within the meaning of the invention, are particles that contain no or only small amorphous fractions and are therefore primarily crystalline. According to an embodiment of the present invention, the crystallinity of the product particles is greater than that of micronizates. The crystalline proportion of the product particles is ≥98 wt. % according to an embodiment of the present invention and can comprise ≥99 wt. % and ≥99.9 wt. % according to other embodiments of the present invention.

Crystallinity is determined by means of X-ray powder diffractometry (XRPD). In this, the integral intensities in the X-ray diffraction pattern are compared, after background correction, with those of a reference material. This reference material can for example be a conventional micronizate or a product obtained by another production process with known crystallinity and comparable granulometry. The crystallinity is thus a relative quantity, which characterizes the degree of order in comparison with a reference sample. The ratio of the integral reflection intensities of particle sample and reference sample is therefore the quantitative expression for their difference in crystallinity.

According to an embodiment of the present invention, the crystallinity of the primary particles is also greater than that of micronizates. The primary particles can comprise a crystallinity is ≥98 wt. %, ≥99 wt. %, and ≥99.9 wt. % according to various embodiments of the present invention. According to an embodiment of the present invention, the product particles are used as primary particles from previous production, in particular from previous production by the method according to the invention. In this configuration, the primary particles have the same properties as the product particles, i.e. primary and product particles are identical. The surface area of the primary particles used and of the crystals obtainable according to an embodiment of the present invention can comprise 3-10 $m^2/g$, preferably 4-8 $m^2/g$. Owing to the very large crystal surface made available during crystallization, a high level of supersaturation in the system of solvent and non-solvent, even with slowly crystallizing active substances, is rapidly reduced in the metastable region and renewed nucleation is therefore suppressed. The added dissolved active substance therefore crystallizes primarily on existing crystal surfaces.

According to an embodiment of the present invention, the primary particles of the active substance are used in the form of a suspension. In particular, providing the primary particles and the inert formed pieces in a suspension of solvent and non-solvent and add the solution of the active substance and the non-solvent is particularly advantageous.

The product particles can be separated with usual methods, for example by filtration. A suspension of product particles can be taken from the crystallization mixture. According to an embodiment of the present invention, the method comprises adding (a) a solution of the active substance in the solvent and (b) non-solvent to a suspension of primary particles of the active substance and inert formed pieces in a mixture of solvent and non-solvent for the active substance; mixing the suspension by stirring, the crystallizing active substance out of the suspension; separating the active substance in the form of product particles; and drying the product particle; wherein the product particles are crystalline, with a crystallinity of ≥98 wt. %, in particular ≥99 wt. % according to an embodiment of the present invention, are in the most stable crystal modification of the active substance, have a crystal surface area of 3-10 $m^2/g$ and the size distribution of the product particles is $d_{50}$=1-2 μm, $d_{99}$<6 μm and $d_{100}$<12 μm.

Through the mixing of the suspension, the solids contained in the suspension, i.e., the particles of active substance (primary and product particles) and the inert formed pieces, are moved. This leads to an especially intensive mixing of the suspension, thus avoiding formation of zones with different degrees of supersaturation of the active substance. The concentration of the active substance in the liquid of the suspension is therefore essentially constant spatially. An exception to this is the place of addition of the solution of active substance. To avoid high levels of supersaturation it is further preferable to add the solution of active substance and the non-solvent to the suspension at different places. Addition can also be carried out via distributing nozzles, hollow stirrers or other devices supporting rapid and uniform distribution throughout the volume of the suspension. By avoiding local differences in supersaturation, particularly uniform crystallization and a narrow particle size distribution are achieved.

The mixing of the suspension can be carried out by stirring, shaking, rotation, ultrasound treatment, passing gases through, recirculation of the suspension by pumping and other methods of mixing known to a person skilled in the art. Stirring of the suspension is preferred. Mixing takes place by keeping the solid particles (particles and formed pieces) in motion. Plug flow does not develop in the suspension during mixing, in which the quality of mixing is different in the axial and radial direction; on the contrary, the stirring device is selected so that mixing takes place as intensively and homogeneously as possible, to avoid different degrees of supersaturation in the suspension. When using a stirring device, the energy input at usual stirring speeds in a stirred reactor is sufficient for the very narrow particle size distribution according to the invention. Depending on the type and size of the stirrer used, stirring speeds of 200-2500 rpm, in particular 500-2000 rpm (revolutions per minute), are preferred. The associated energy input at usual stirring speeds is a long way from the usual specific energy inputs in ball mills or high-pressure homogenizers, so that there are hardly any contamination problems through abrasion and the disadvantages of comminution methods described above are avoided, in particular nanofractions and amorphization are minimized.

The combination of primary particles used, inert formed pieces and mixing of the suspension surprisingly has the effect that the particle size of the product particles, despite the crystal growth—oriented procedure of the method according to the invention, does not increase over an extended period, as the crystal surface lost via the product particles is compensated for by secondary nucleation, mainly promoted by the inert formed pieces. In contrast to a nucleation—oriented crystallization with high levels of supersaturation and without primary particles, the method according to the invention is a growth-oriented crystallization, in which the active substance mainly crystallizes on crystal surfaces that are already present.

Owing to the growth orientation of the method according to the invention, it is suitable in particular for poorly or sluggishly crystallizing substances, in particular those that tend to pass through intermediate forms, for example oils or thermodynamically less stable crystal forms. In the course of the method, in particular when product particles are removed repeatedly in batches or continuously over an extended period, the product particles take over the role of the primary particles that are present at the start of the process. Without primary particles, however, the course of the crystallization process and therefore the quality of the product particles often cannot be controlled as desired, because without the primary particles as a rule wide particle size distributions, in particular more nanofractions are generated, often the desired, most stable crystal modification is not obtained and/or there is a large amorphous fraction.

The residence time in the suspension in the crystallization device can be >12 min, >15 min >20 min according to varying embodiments of the present invention. In this way especially narrow product particle size distributions and low levels of amorphization are obtained. The residence time is the average time that a volume element remains in the suspension. The inert formed pieces preferably remain in the suspension and so are not removed with the product particles.

In the method according to the invention, the inert formed pieces perform, among other things, the role of promoting secondary nucleation, by which new crystal particles form and the proportion of larger product particles is minimized by crystallization on existing particles (primary and product particles) or by agglomeration in the suspension. "Inert" means, in this context, that the formed pieces do not dissolve in the solvent for the active substance or in the non-solvent, and produce no or only very little abraded material during mixing, for example as a result of stirring of the crystallization suspension. The formed pieces can be of various shapes, for example spherical, oval, cylindrical or star-shaped, spherical formed pieces being preferred. The formed pieces are preferably made of abrasion-resistant, hard materials, for example zirconium oxide or silicon carbide. The formed pieces can also comprise Yttrium-stabilized zirconium oxide spheres according to an embodiment of the present invention. Inert formed pieces with a maximum size of 0.1-2 mm have proved favorable, preferably 0.2-1 mm, for example inert microspheres with a diameter of 0.2-1 mm can be used. It has also proved favorable if the proportion of inert formed pieces, relative to the total volume of the crystallization suspension, is approximately 20-80 vol. %, preferably 30-70 vol. %. The weight ratio of particles of active substance (primary and product particles) to formed pieces in the suspension can comprise 1:1000 to 1:10, in particular 1:200 to 1:20 according to embodiments of the present invention.

In order to keep the proportions of solvent low and to keep the solids concentration and therefore the available crystallization surface at a high level, crystallization can be coupled to a parallel distillation/rectification. The pressure conditions are then selected according to the optimum process temperature for crystallization. However, it is also possible to concentrate the suspension after crystallization by evaporation or filtration.

The method according to the invention can be carried out as a batch process or continuously. In batch mode, the solution of the active substance and the non-solvent are added discontinuously, i.e. batchwise, and product particles are removed batchwise, in particular in the form of a suspension of product particles. The continuous mode is preferred, in which a solution of the active substance and non-solvent are added continuously and a suspension of product particles is removed continuously. The inert formed pieces remain in the crystallization vessel.

Both in the batch mode and in the continuous mode of the crystallization process according to the invention it is preferable for the volume of the crystallization suspension to remain substantially constant, as an especially uniform grain size distribution can then be achieved. "Substantially constant" means, in this context, that the volume of the suspension does not vary by more than 20 vol. %. The volume of the suspension, relative to the mean value of the volume (100% value), is preferably 90-110 vol. %, in particular 95-105 vol. %.

The solution of the active substance can comprise one or more solvents for the active substance. Suitable solvents are in particular alcohols, ketones and ethers, for example methanol, ethanol, isopropanol, acetone and diethyl ether. Water is preferably used as non-solvent. A non-solvent is, within the meaning of the invention, a liquid in which the active substance is poorly soluble. The solubility should be less than 0.5 g of active substance per liter of non-solvent.

The solubility of the active substance in the solvent is preferably above 10 g/L, and the solubility in the non-solvent is preferably less than 0.1 g/L according to an embodiment of the present invention. Alternatively, the solubility of the active substance in the solvent can be above 100 g/L, while the solubility in the non-solvent is less than 0.1 g/L or less than 0.05 g/L according to another embodiment of the present invention. The quantitative ratio of non-solvent to solvent depends on the solubility function of the active substance in the solvent/non-solvent system. A volume ratio of solvent to non-solvent can comprise 1:1 to 1:10. Solvent and non-solvent should be miscible in the quantitative ratio used, i.e. can form a homogeneous mixture.

The product particles can be dried by the usual methods, for example by spray-drying, lyophilization or other types of solvent evaporation, spray-drying being preferred, in particular by nozzle or disk atomizing, as this has hardly any effect on the size of the individual particles and hence the size distribution. The size distributions described above therefore also preferably apply to the dried product particles.

The active substance can comprise a steroid, a steroid hormone such as a gestagen or an oestrogen, or an antiasthmatic, such as a glucocorticoid. A steroid is a compound that has the carbon structure of perhydrogenated cyclopenta[a]phenanthrene. According to an embodiment of the present invention, the active substance can be selected from the group comprising drospirenone, desogestrel, dienogest, ethinylestradiol, fluticasone and budesonide. Drospirenone and fluticasone are the most preferred.

A hydrophilic, pharmaceutically acceptable excipient can be added, as solution, for example in water, to the product particles before drying, in order to produce a solid form of particles of active substance, which supports the release of the particles of active substance from the solid form and later from the pharmaceutical form on contact with water. Hydrophilic excipients are to be understood as excipients that are soluble in water.

Mainly water-soluble hydroxyalkylcelluloses, in particular hydroxyethylcellulose, hydroxypropylcellulose and hydroxypropylmethylcellulose, and polyvinylpyrrolidone and similar excipients also usual in tablet production, may be considered as hydrophilic, pharmaceutically acceptable excipients. Other excipients can also be added, for example excipients that promote release or protect the active substance. The proportion of the excipient depends on the extent to which the rapid release of the particles of active substance from the solid body described above is achieved. The proportion of the hydrophilic, pharmaceutically acceptable excipient is preferably between 20 and 90 wt. %, in particular between 40 and 75 wt. %, relative to the total weight of the solid form of particles of active substance.

Very small microparticles, in particular those of hydrophobic active substances, show poor wetting in contact with water and under the influence of van der Waals forces they tend to form loose agglomerates, which prevent rapid dissolution. These agglomerates may in certain circumstances also form in the suspension of the method according to the invention after removal from the crystallizer, as a function of time, residual supersaturation and physicochemical properties of the active substance. Therefore maximum possible elimination of supersaturation and prompt further processing may be desirable. Accordingly, an embodiment of the present invention is a continuous process, in which, immediately after continuous removal of the suspension of product particles, a hydrophilic excipient is added, preferably in the form of a solution. This can for example be added as excipient solution in a mixing line, the suspension being mixed homogeneously with excipient supplied to a stirred vessel for buffering and then spray-dried. In this way a possible, subsequent agglomeration can largely be prevented.

According to an embodiment of the present invention, the solid form of the particles of active substance can be produced by spray-drying of the particle suspension with subsequent separation of the powder with a product filter. In the spray-drying process, a solid is formed, which contains the particles of active substance. The solid form can comprise hollow microparticles of the excipient, with the individual particles of active substance embedded in their surface. As a result, in contact with water the very rapid, particulate release of the active substance crystals is supported, often within 1-3 minutes (cf. Example 3). The precondition for their very rapid dissolution is thus provided. In vitro, according to the paddle test, complete dissolution in water at 37° C. and 25% saturation concentration of the active substance was achieved within 5 min.

The dissolution rate is largely independent of the grain size of the solid. Therefore the grain size only has an upper limit for fulfilling uniformity of content in the pharmaceutical form. The solid form of particles of active substance preferably has a size distribution with $d_{50}<20\,\mu m$ and $d_{100}<200\,\mu m$. The solid form of active substance according to the invention can, if this is advantageous for the pharmaceutical application, while retaining the fast release properties, also be produced with a reduced nanofraction. Using spray-drying technology, grain sizes, as well as other properties can be adjusted well to the pharmaceutical application, for example by adding other additives, excipients or fillers.

The excipient particles of the solid form of particles of active substance according to the invention disintegrate in water preferably within 3 min, in particular within one minute. In this way the solid form of particles of active substance releases the particles of active substance within 3 min, in particular within one minute, without aggregation. In their turn, the particles of active substance according to the invention dissolve in water after their release from the solid form or in pure form according to the USP paddle test (paddle test according to the USP method) within 10 min to >95 wt. %, preferably within 5 min to >95 wt. %.

According to an embodiment of the present invention, in the paddle test according to the USP method the crystalline particles of active substance according to the invention therefore release at least 95 wt. % of the active substance in 10 min, preferably in 5 min. "Release" means, in this context, that the active substance dissolves in water. In another embodiment of the present invention, in the paddle test according to the USP method the solid form of particles of active substance according to the invention releases at least 95 wt. % of the active substance in 13 min, preferably in 8 min, especially preferably in 6 min.

According to the WHO definition (Bio Waiver), very fast release dosage forms should release at least 85% of the active substance in 15 min, and fast release dosage forms should release at least 85% of the active substance in 30 min. The crystalline microparticles of active substance and the solid form of particles of active substance of the present invention are therefore especially suitable for fast release and in particular very fast release dosage forms.

The crystallization process according to the invention can be carried out in a device that is of simple design and is inexpensive. The method is preferably carried out in a heatable and coolable stirred crystallizer, which is partially filled with the formed pieces, which are inert with respect to the used solvent, non-solvent and active substances. The crystallizer can be provided with a distillation or rectification attachment and a distillate receiver. Moreover, the device for crystallization comprises feed lines for the solution of active substance and the non-solvent, and a discharge line for removing the product particles. The feed lines can be designed so as to promote the quickest possible distribution of solution of active substance and non-solvent in the suspension volume, e.g. distributing nozzles can be provided. The stirrer itself can also be used as a feed line for one component, e.g. for the solution of active substance, if it is constructed as a hollow stirrer and the liquid is led via the hollow shaft and the stirrer blades directly into the turbulent shearing field of the stirrer. There is therefore very rapid and homogeneous distribution of the dissolved active substance throughout the reactor volume, and high local supersaturations, which can lead to nucleation showers, are quickly cancelled. The discharge line can be provided with filtration elements or sedimentation zones for recycling inert formed pieces back into the stirred crystallizer. Furthermore, the discharge line can contain a mixing device, for example a stationary mixer, and an additional feed line can be connected to the mixer, if a solution of the excipient is to be supplied in the next step. Optionally, the discharge line can contain a device for concentrating the suspension, for example an evaporator or a filtration device. The discharge line then leads to the drying device, which is in particular a spray-dryer. If solid forms of the active substance particles are to be produced, the discharge line first opens into a stirred vessel, which can also function as a mixing device, in which the pharmaceutical excipient and the product particles are mixed. From there, a feed line leads to the drying device, for example a two-substance nozzle or an atomizing disk of a spray-dryer.

The invention also relates to crystalline microparticles of active substance, obtainable by the method described above. The invention also relates to crystalline microparticles of active substance, in which the microparticles are crystalline, are in the most stable crystal modification, have a crystal surface area of 3-10 $m^2/g$ and the size distribution of the microparticles is $d_{50}=1-2\,\mu m$, $d_{99}<6\,\mu m$ and $d_{100}<12\,\mu m$. The invention further relates to a solid form of an active substance, comprising a hydrophilic, pharmaceutically acceptable excipient and the crystalline microparticles of active substance described above.

The embodiments of the product particles and the solid form of particles of active substance described above in connection with the method according to the invention also apply to the crystalline microparticles of active substance according to the invention and the solid form of the active substance. According to an embodiment of the present invention, the crystallinity of the microparticles of active substance is greater than that of micronizates. The crystallinity, i.e. the crystalline fraction, can comprise ≥98 wt. %, ≥99 wt. % and ≥99.9 wt. % according to an embodiment of the present invention.

The invention also relates to the use of the crystalline microparticles of active substance described as a medicament and for the production of medicaments, preferably for pulmonary applications, and the use of the solid form of particles of active substance as a medicament and for the production of medicaments. For this, the crystalline microparticles of active substance or the solid form of particles of active substance according to the invention are optionally processed with additives, excipients, fillers, lubricants etc., known to a person skilled in the art, into a medicament.

For pulmonary applications, the bioavailability depends not only on rapid dissolution, but also on the particle size being as far as possible within a specified range, preferably between 1 and 5 μm, as otherwise the particles of active substance do not get into the lung or alternatively are exhaled again. Here, the method according to the invention offers the particular advantage that not only the maximum grain size can be limited, but also the fraction of fine grains in the nano range can be reduced.

In the case of active substances for pulmonary application, e.g. antiasthmatics for dry powder inhalers (DPI), the pure active substance does not comprise excipients. In these cases addition of excipients is therefore omitted. By spray-drying, preferably by nozzle atomizing, any loose agglomerates are broken up and the fine primary grains of the active substance are transformed to the powder state without increasing the coarseness of the suspension. By limiting the nanofraction, and owing to the high crystallinity of the DPI active substance, moreover the stability and dispersibility are improved.

The following examples describe embodiments of the present invention.

Example 1

A 100-ml stirred vessel with blade stirrer is charged with 160 g of Y-stabilized zirconium oxide spheres with a diameter of 0.5 mm plus 30 ml water. A solution of 1.5 g drospirenone in 6.25 ml ethanol/water 4:1 (v/v) is added, with stirring. After precipitation of a mainly amorphous phase, transformation to the crystalline modification begins after approximately 2 min. This is completed after 10 to 15 min. After completion of the phase transformation, a solution of 4.5 g drospirenone in 18.75 ml ethanol/water 4:1 (v/v) and in the same ratio 90 ml water is added dropwise within 15 min, with stirring at 1500 rpm. Simultaneously, with approximately constant filling level, product suspension is drawn off. Addition and product withdrawal can also take place quasicontinuously in smaller portions without any adverse effect on the result, if the above time frame is maintained. After the end of addition, to make the yield complete, approx. 60 ml water is used for rinsing. Alternatively, the suspension in the crystallizer can also be left as starting suspension for the next batch. Altogether, 200 g of suspension is obtained, with a solids content of 25 mg per ml. Approximately 15 ml of this suspension is filtered on a G4 frit and the solid is air-dried. The grain size distribution of the dried substance is determined by laser diffraction (Sympatec Helos, RODOS dispersing system).

Result: $d_{16}$=0.52 μm, $d_{50}$=1.48 μm, $d_{99}$=4.63 μm, $d_{100}$=6.00 μm

Example 2

Spray-Drying+Granulometric Analysis of the Solid Form 15 g of hydroxypropylmethylcellulose (HPMC) Methocel E5 is added to 200 g of the aqueous suspension according to Example 1 and stirred until the HPMC has dissolved completely. The suspension is spray-dried in a Yamato/QVF GA32 laboratory spray-dryer by means of a two-substance nozzle under the following conditions:

Feed: 4-5 g/min
Drying air: 0.5 m³/min
Nozzle pressure: 2.5 bar (gauge)
Inlet temperature: 180° C.
Outlet temperature: 70-75° C.
8 g of product powder is separated in a product filter
Granulometric analysis is carried out by laser diffraction (Sympatec Helos, RODOS dispersing system):
$d_{16}$=2.0 μm, $d_{50}$=5.2 μm, $d_{99}$=17.4 μm, $d_{100}$=20.6 μm Example 3

Release of Primary Particles From the Solid Form (Micrographs)

Figure 1:
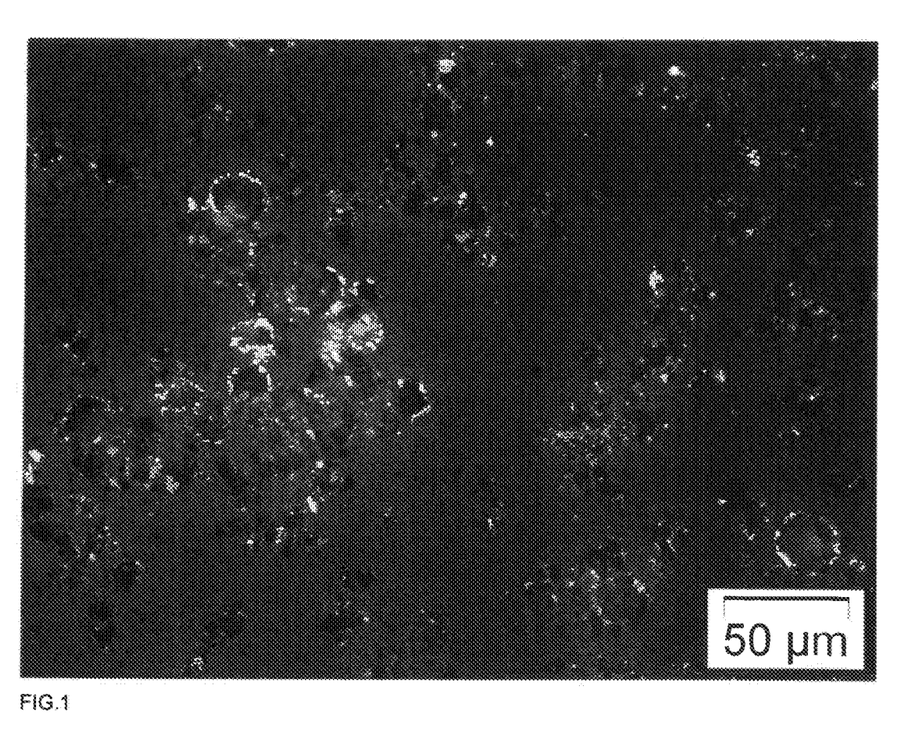
FIG. 1 is a light micrograph of the solid form of particles of active substance according to an embodiment of the present invention.
Figure 2:
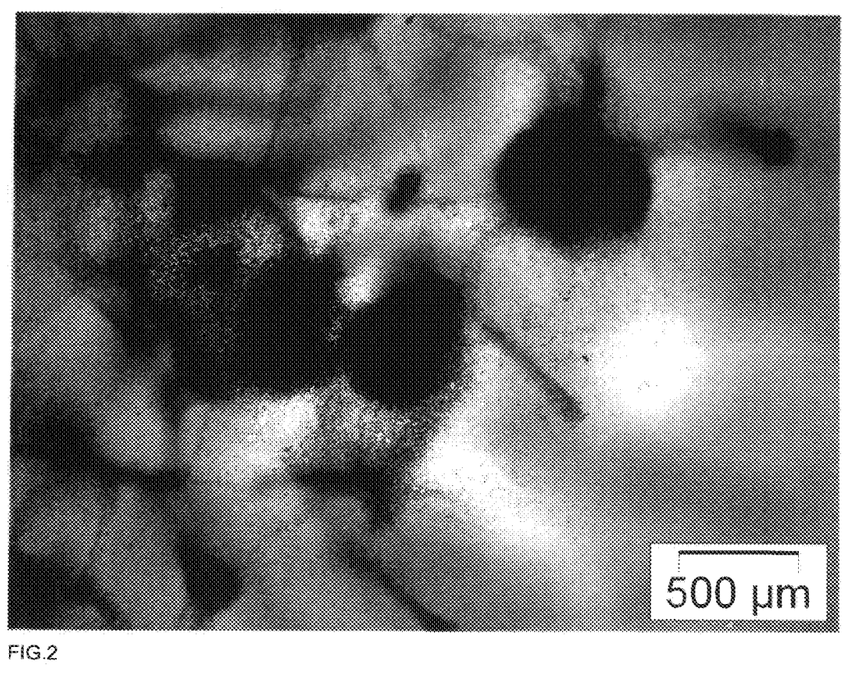
FIG. 2 is a light micrograph of the release process of the solid form of particles of active substance according to an embodiment of the present invention immediately after contact with water.
Figure 3:
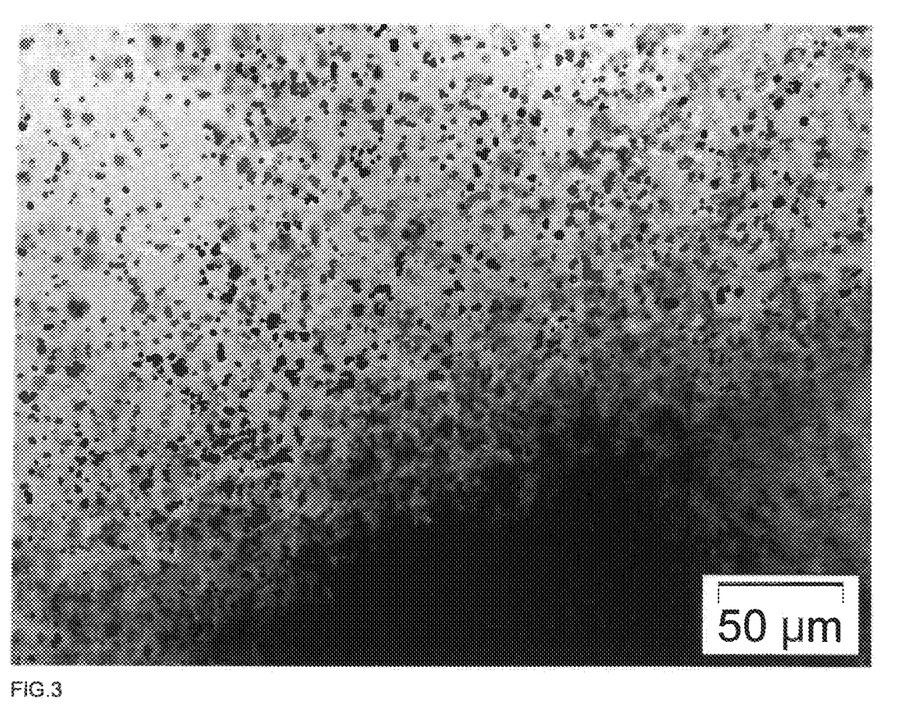
FIG. 3 is a light micrograph of the release process of the solid form of particles of active substance according to an embodiment of the present invention immediately after contact with water.
Figure 4:
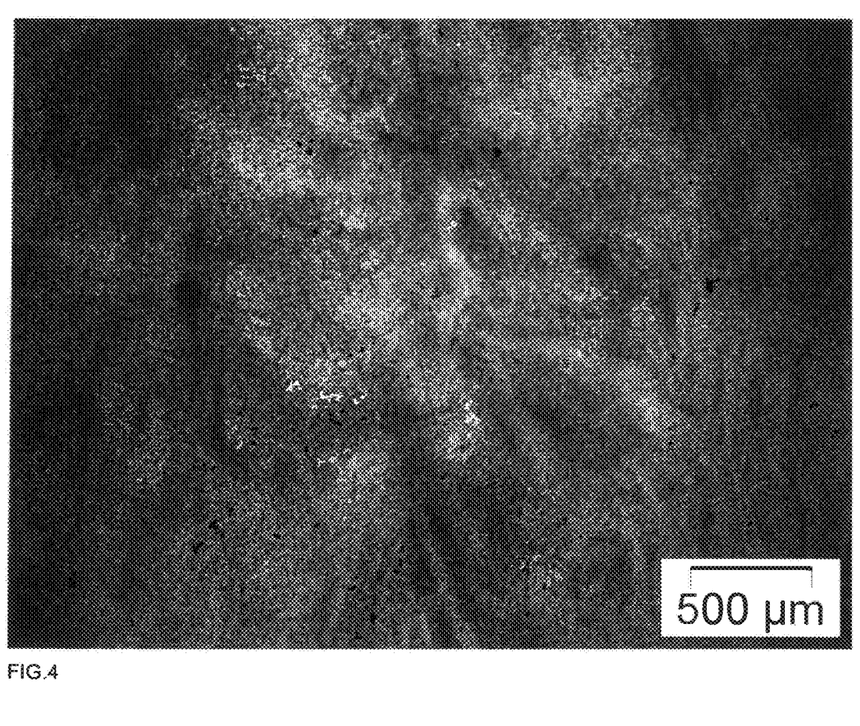
FIG. 4 is a light micrograph of the release process of the solid form of particles of active substance according to an embodiment of the present invention three minutes after contact with water.
Figure 5:
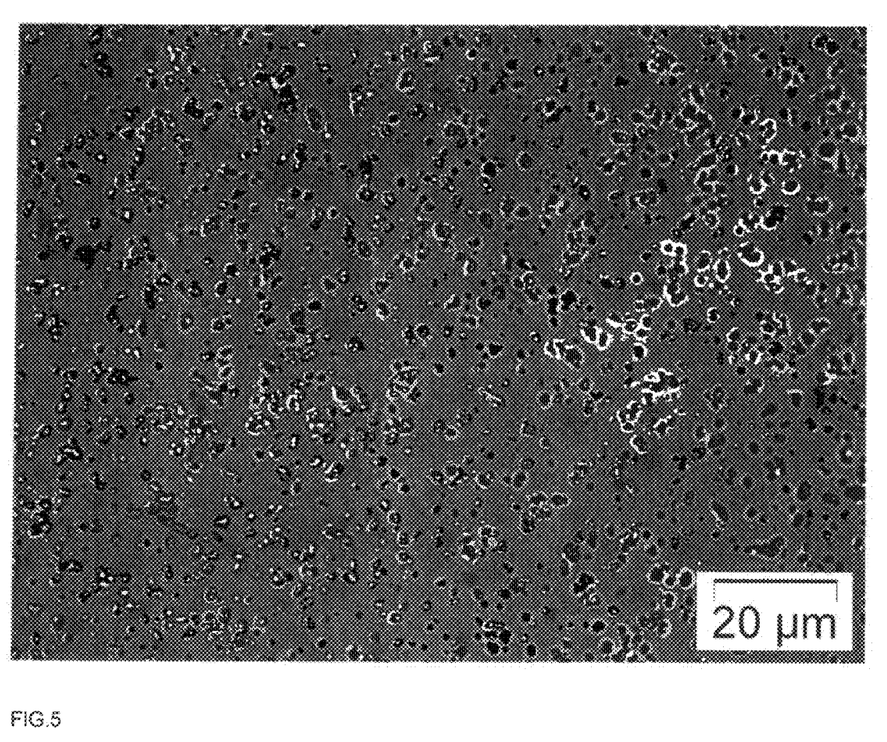
FIG. 5 is a light micrograph of the release process of the solid form of particles of active substance according to an embodiment of the present invention three minutes after contact with water.

A small amount of the solid form according to Example 2 is placed on the motionless surface of water. The disintegration process of the solid form is observed under a transmitted-light microscope. FIG. 1 shows the spray-dried solid form. The primary particles of the active substance, readily discernible under polarized light, are embedded in the surface of the spherical HPMC particles. FIG. 2 to FIG. 5 show the individual phases of the release process. It is shown that whereas the excipient goes into solution, the particles of active substance are released as particles without aggregation within 1-3 min on a motionless water surface. This process can be speeded up by stirring.

Example 4

Figure 6:
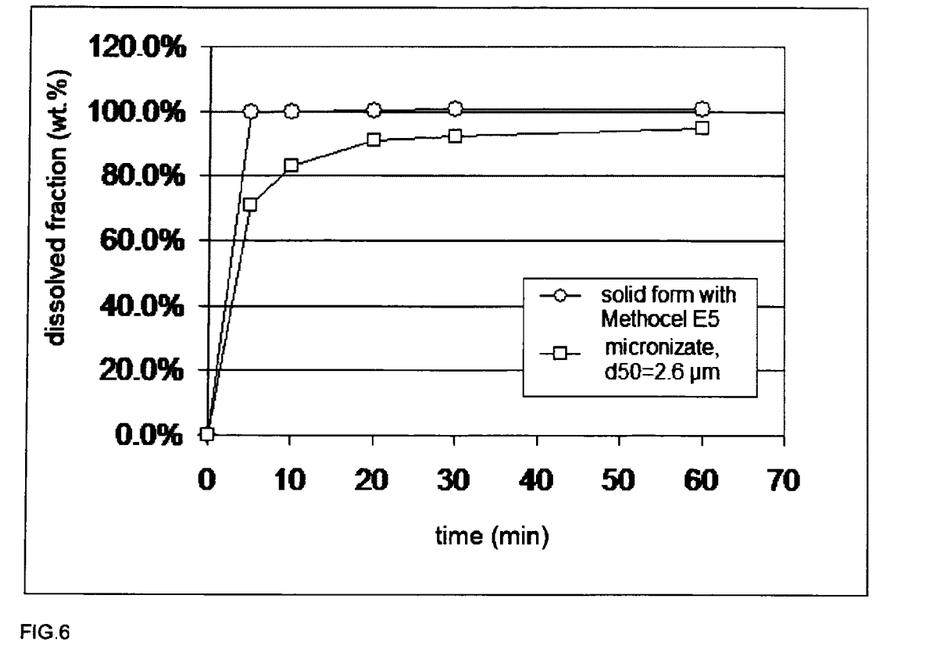
FIG. 6 is a light micrograph of the release of drospirenone from the solid form of particles of active substance according to an embodiment of the present invention as compared with a conventional micronizate.

Solubility Kinetics of the Solid Form with Methocel E5 by the Paddle Method 14 mg of the solid form with Methocel E5 as excipient according to Example 2 with a content of active substance of 21.5 wt. % (equivalent to 3 mg drospirenone) is added to 900 ml water, at 37° C. and stirred at 150 rpm with a blade stirrer. A blind sample (starting value) and samples at 5, 10, 20, 30, and 60 min are taken, filtered in a 0.2 μm syringe filter and the dissolved fraction of drospirenone is determined by HPLC. A conventional micronizate (jet mill) serves as comparison. So that the dissolution behavior of the primary grains of the micronizate is assessed exclusively, wetting and agglomeration effects must be avoided. Therefore, before it was added to the 900 ml of water, the micronizate was dispersed in 2 ml of a PVP-containing solution. The results of release are shown in FIG. 6. The process of release of the particles from the solid form and the subsequent process of dissolution are completed after 5 min, whereas with the conventional micronizate, even with perfect wetting and dispersion of the particles, still almost 30% of the active substance is undissolved after 5 min.

Example 5

Fluticasone for Pulmonary Application; Crystallization and Spray-Drying without Excipients A 100-ml stirred vessel with blade stirrer is charged with 160 g of Y-stabilized zirconium oxide spheres with a diameter of 0.5 mm plus 30 ml of water. A solution of 0.6 g fluticasone in 10 ml acetone is added with stirring. After stirring for 5 min, a solution of 1.8 g fluticasone in 30 ml acetone and in the same ratio 90 ml water are added dropwise within 10 min, with stirring at 1300 rpm. Simultaneously, product suspension is drawn off, with approximately constant filling level. Addition and product withdrawal can also take place quasi-continuously in smaller portions without any adverse effect on the result, if the above time frame is maintained. After addition, to complete the yield it is rinsed with approx. 60 ml water. According to an embodiment of the present invention, the suspension in the crystallizer can be left as starting suspension for the next batch. Altogether, 180 g of suspension with a solids content of 13 mg per ml is obtained. The suspension is spray-dried in a Yamato/QVF GA32 laboratory spray-dryer by means of a two-substance nozzle under the following conditions:

Feed: 6 g/min
Drying air: 0.3 m$^3$/min
Nozzle pressure: 3 bar (gauge)
Inlet temperature: 170-180° C.
Outlet temperature: 65-75° C.

1.5 g of product powder is separated in a product filter.

Granulometric analysis was carried out by laser diffraction (Sympatec Helos, RODOS dispersing system, dispersing pressure 5 bar).

Result: $d_{10}$=0.5 µm, $d_{50}$=1.47 µm, $d_{99}$=4.80 µm, $d_{100}$=6.00 µm

Determination of Crystallinity:
Measuring method: XRPD (X-ray powder diffraction)
Instrument: Siemens D5000 (fixed sample position) with Euler balance and secondary monochromator
Bragg-Brentano arrangement
Cu/CuKα radiation
Tube voltage: 40 kV
Tube current 30 mA
2θ range: 5-60° C.
Step width: 0.03°
Evaluation software: EVA Diffrac AT (Bruker AXS)
Crystallinity compared with the conventional jet mill micronizate:
Jet mill micronizate: 95 wt. %
Fluticasone: 100 wt. %

Although specific examples have been illustrated and described herein, it will be appreciated by those of ordinary skill in the art that any arrangement calculated to achieve the same purpose could be substituted for the specific examples shown. This application is intended to cover adaptations or variations of the present subject matter. Therefore, it is intended that the invention be defined by the attached claims and their legal equivalents, as well as the following illustrative embodiments.

The invention claimed is:

1. A method for producing crystalline microparticles of a hydrophobic active substance, the method comprising:
preparing a suspension from primary particles of the hydrophobic active substance, the suspension comprising a solution of the hydrophobic active substance in a solvent having a solubility greater than 10 g/L, a non-solvent having a solubility less than 0.5 g/L for the hydrophobic active substance, and inert formed pieces having a particle size between 0.1-2 mm that do not dissolve in the solvent for the solution of the hydrophobic active substance or the non-solvent for the hydrophobic active substance, wherein a proportion of the inert formed pieces relative to the total volume of the suspension is about 20-80 vol. %, and wherein the primary particles of the hydrophobic active substance are crystalline and in the most stable crystal modification of the hydrophobic active substance;
mixing the prepared suspension to cause crystallization of the hydrophobic active substance out of the suspension forming a crystallization mixture;
separating the hydrophobic active substance in the form of particles; and
drying the product particles, wherein the primary particles and the product particles are crystalline, are in the most stable crystal modification of the hydrophobic active substance, have a crystal surface area of 3-10 m$^2$/g and the size distribution of the primary and product particles is each $d_{50}$=1-2 µm, $d_{99}$<6 µm and $d_{100}$<12 µm.

2. The method of claim 1, wherein the solution of the hydrophobic active substance in the solvent and the non-solvent are added to a suspension of the primary particles, the inert formed pieces in a mixture of solvent and non-solvent for the hydrophobic active substance.

3. The method of claim 1 further comprising:
separating the product particles by removing a suspension of product particles from the crystallization mixture.

4. The method of claim 1, wherein mixing the prepared suspension is performed by stirring the suspension.

5. The method of claim 1, wherein the $d_{10}$ of the product particles is <0.7 µm and $d_{100}$ of the product particles is <8 µm.

6. The method of claim 1, wherein the crystallinity of the primary particles and of the product particles is each ≥98 wt. %.

7. The method of claim 1, wherein the suspension does not contain any other excipients.

8. The method of claim 1, wherein the hydrophobic active substance is a steroid hormone or glucocorticoid selected from the group consisting of drospirenone, desogestrel, dienogest, ethinylestradiol, fluticasone and budesonide.

9. The method for producing a solid form of particles of hydrophobic active substance, comprising a method according to claim 1, in which additionally a hydrophilic, pharmaceutically acceptable excipient is added to the separated product particles prior to drying.

10. Crystalline microparticles of a hydrophobic active substance prepared by a process comprising the steps of:
preparing a suspension from primary particles of the hydrophobic active substance, the suspension comprising a solution of the hydrophobic active substance in a solvent having a solubility greater than 10 g/L, a non-solvent having a solubility less than 0.5 g/L for the hydrophobic active substance, and inert formed pieces having a particle size between 0.1-2 mm that do not dissolve in the solvent for the solution of the hydrophobic active substance or the non-solvent for the hydrophobic active substance, wherein a proportion of the inert formed pieces relative to the total volume of the suspension is about 20-80 vol. %, and wherein the primary particles of the active substance are crystalline and in the most stable crystal modification of the active substance;
mixing the prepared suspension to cause crystallization of the hydrophobic active substance out of the suspension;
separating the hydrophobic active substance in the form of particles; and
drying the product particles, wherein the primary particles and the product particles are crystalline, are in the most stable crystal modification of the hydrophobic active substance, have a crystal surface area of 3-10 m$^2$/g and the size distribution of the primary and product particles is each $d_{50}$=1-2 µm, $d_{99}$<6 µm and $d_{100}$<12 µm.

11. The crystalline microparticles of claim 10, wherein the microparticles are crystalline, are in the most stable crystal modification of the hydrophobic active substance, have a crystal surface area of 3-10 m$^2$/g and the size distribution of the microparticles is $d_{50}$=1-2 µm, $d_{99}$<6 µm and $d_{100}$<12 µm.

12. The crystalline microparticles of the hydrophobic active substance of claim 10, wherein the size distribution of the microparticles is $d_{10}$ is <0.7 μm, $d_{50}$=1-2 μm and $d_{100}$<8 μm.

13. The crystalline microparticles of the hydrophobic active substance of claim 10, wherein the crystallinity of the crystalline microparticles is ≥98 wt. %.

14. The crystalline microparticles of the hydrophobic active substance of claim 10, wherein the microparticles do not contain other excipients.

15. Crystalline microparticles of the hydrophobic active substance of claim 10, wherein the active substance is a steroid hormone or a glucocorticoid.

16. Solid form particles comprising crystalline microparticles of a hydrophobic active substance and a hydrophilic, pharmaceutically acceptable excipient, the solid form particles formed by a method comprising:
preparing a suspension from primary particles of the hydrophobic active substance, the suspension comprising a solution of the hydrophobic active substance in a solvent having a solubility greater than 10 g/L, a non-solvent having a solubility less than 0.5 g/L for the hydrophobic active substance, and inert formed pieces having a particle size between 0.1-2 mm that do not dissolve in the solvent for the solution of the hydrophobic active substance or the non-solvent for the hydrophobic active substance, wherein a proportion of the inert formed pieces relative to the total volume of the suspension is about 20-80 vol. %, and wherein the primary particles of the active substance are crystalline and in the most stable crystal modification of the active substance;
mixing the prepared suspension to cause crystallization of the hydrophobic active substance out of the suspension,
separating the hydrophobic active substance in the form of product particles,
adding the hydrophilic, pharmaceutically acceptable excipient in a solution to the product particles, and
drying the product particles and the hydrophilic, pharmaceutically acceptable excipient to produce the solid form of particles of the hydrophobic active substance, wherein the primary particles and the product particles are crystalline, are in the most stable crystal modification of the hydrophobic active substance, have a crystal surface area of 3-10 m²/g and the size distribution of the primary and product particles is each $d_{50}$=1-2 μm, $d_{99}$<6 μm and $d_{100}$<12 μm.

17. Solid form of particles of active substance according to claim 16, wherein the hydrophilic excipient is selected from the group consisting of hydroxyalkylcellulose, hydroxyethylcellulose, hydroxypropylcellulose, hydroxypropylmethylcellulose and polyvinylpyrrolidone.

18. The crystalline microparticles of active substance according to claim 10, wherein the microparticles are in a medicament for pulmonary applications.

19. Solid form of particles of active substance according to claim 11, wherein the solid form of particles are in a fast release dosage form of a medicament.

20. Crystalline microparticles of active substance of claim 15, wherein the active hydrophobic substance is selected from the group consisting of drospirenone, desogestrel, dienogest, ethinylestradiol, fluticasone and budesonide.

21. A pharmaceutically active substance comprising:
a plurality of crystalline microparticles of a hydrophobic active substance, wherein the plurality of crystalline microparticles of the hydrophobic active substance have a crystalline form, the plurality of crystalline microparticles of the hydrophobic active substance are in the most stable crystal modification of the hydrophobic active substance, the plurality of crystalline microparticles of the hydrophobic active substance have a crystal surface area of 3-10 m²/g, and the plurality of crystalline microparticles of the hydrophobic active substance have a size distribution of $d_{50}$=1-2 μm, $d_{99}$<6 μm and $d_{100}$<12 μm.

22. The pharmaceutically active substance of claim 21, wherein the plurality of crystalline microparticles of the hydrophobic active substance have a size distribution of $d_{10}$ is <0.7 μm, $d_{50}$=1-2 μm and $d_{100}$<8 μm.

23. The pharmaceutically active substance of claim 21, wherein the crystallinity of the crystalline microparticles is ≥98 wt. %.

24. The pharmaceutically active substance of claim 21, wherein the crystallinity of the crystalline microparticles is ≥99 wt. %.

25. The pharmaceutically active substance of claim 21, wherein the microparticles do not contain other excipients.

26. The pharmaceutically active substance of claim 21, wherein the hydrophobic active substance is a steroid hormone or a glucocorticoid.

27. The pharmaceutically active substance of claim 26, wherein the hydrophobic active substance is selected from the group consisting of drospirenone, desogestrel, dienogest, ethinylestradiol, fluticasone and budesonide.

* * * * *